United States Patent [19]

Clark et al.

[11] Patent Number: 5,347,496
[45] Date of Patent: Sep. 13, 1994

[54] METHOD AND SYSTEM OF MAPPING ACOUSTIC NEAR FIELD

[75] Inventors: Joseph A. Clark, Arlington; Michael A. Sartori, McLean, both of Va.

[73] Assignee: The United States of America as represented by the Secretary of the Navy, Washington, D.C.

[21] Appl. No.: 104,707

[22] Filed: Aug. 11, 1993

[51] Int. Cl.$^5$ .............................................. H04R 17/00
[52] U.S. Cl. .................................... 367/140; 367/191; 181/0.5; 73/645; 73/646
[58] Field of Search .................. 73/645, 646; 367/140, 367/191; 181/0.5

[56] References Cited

U.S. PATENT DOCUMENTS

| | | | |
|---|---|---|---|
| 4,301,684 | 11/1981 | Thompson et al. | 73/602 |
| 4,592,034 | 5/1986 | Sachse et al. | 367/127 |
| 4,648,080 | 3/1987 | Hargreaves | 367/20 |
| 4,658,384 | 4/1987 | Dragoset, Jr. et al. | 367/23 |
| 4,738,138 | 4/1988 | Redman-White | 73/594 |
| 4,955,001 | 9/1990 | Guigne | 367/118 |
| 4,979,124 | 12/1990 | Sachse et al. | 364/507 |
| 5,047,990 | 9/1991 | Gafos et al. | 367/6 |
| 5,172,597 | 12/1992 | Hedeen | 73/646 |

Primary Examiner—J. Woodrow Eldred
Attorney, Agent, or Firm—Charles D. Miller

[57] ABSTRACT

A method and system for mapping the acoustic near field of a stationary axial symmetric structure are provided. The structure is subjected to a rotating excitation energy profile from a plurality of stationary excitation sites located radially around the structure. The acoustic near field of the structure due to the rotating excitation energy profile is measured along at least one line that conforms to a longitudinal surface of the structure. Mapping of the acoustic near field is complete when one rotation of the rotating excitation energy profile is complete.

16 Claims, 5 Drawing Sheets

METHOD AND SYSTEM OF MAPPING ACOUSTIC NEAR FIELD

The invention described herein may be manufactured and used by or for the Government of the United States of America for governmental purposes without payment of any royalties thereon or therefor.

FIELD OF THE INVENTION

The invention relates generally to acoustics, and more particularly to a method and system for mapping the acoustic near field of an axial symmetric structure.

BACKGROUND OF THE INVENTION

The term "acoustic near field" refers to the area of a structure where both radiating and non-radiating (i.e., evanescent) acoustic waves exist. The term "acoustic far field" refers to the area around a structure where only the radiating acoustic waves exist and the non-radiating acoustic waves have decayed. For a given structure producing radiating and non-radiating waves, the radiating waves produce observable responses in the acoustic far field while the non-radiating acoustic waves do not. In mapping the acoustic near field of the structure, both the radiating and non-radiating acoustic waves are measured. Using these measurements and signal processing techniques, information on the types of structural waves traveling along the structure and their contribution to the observable responses in the acoustic far field can be obtained.

To map the acoustic near field of a structure, three measurement techniques have been employed in the prior art. The structure can be moved with respect to a scanning system, the scanning system can be moved with respect to the structure, or the scanning system can include a multitude of measurement devices surrounding the structure. In the first two techniques, the scanning system is a one-dimensional array of measurement devices and either the structure is moved or the array of measurement devices is moved. However, both of these techniques require intricate manipulation and physical coordination between the structure and the scanning system. With the third technique, the scanning system consists of measurement devices located at all positions where measurements of the acoustic near field are desired. The advantage of this technique is that neither the structure nor the measurement devices need be moved. However, this technique is often cost prohibitive as numerous measurement devices are required.

SUMMARY OF THE INVENTION

Accordingly, it is an object of the present invention to provide a method and system for mapping the acoustic near field of a structure that does not require complex coordinated movement between the structure and the scanning system.

Another object of the present invention is to provide a method and system for mapping the acoustic near field of a structure that minimizes the required number of measurement devices.

Other objects and advantages of the present invention will become more obvious hereinafter in the specification and drawings.

In accordance with the present invention, a method and system are provided to map the acoustic near field of an axial symmetric structure. The structure is subjected to excitation energy based on a plurality of repeatable excitation signals at a plurality of stationary excitation sites located radially around the structure. The acoustic near field of the structure is then measured along at least one line that conforms to a longitudinal surface of the structure. This process takes place for each of the excitation signals incrementally provided to each of the stationary excitation sites. The mapping of the acoustic near field is complete when each of the excitation signals has been provided to each of the stationary excitation sites.

DETAILED DESCRIPTION OF THE INVENTION

Figure 1A:
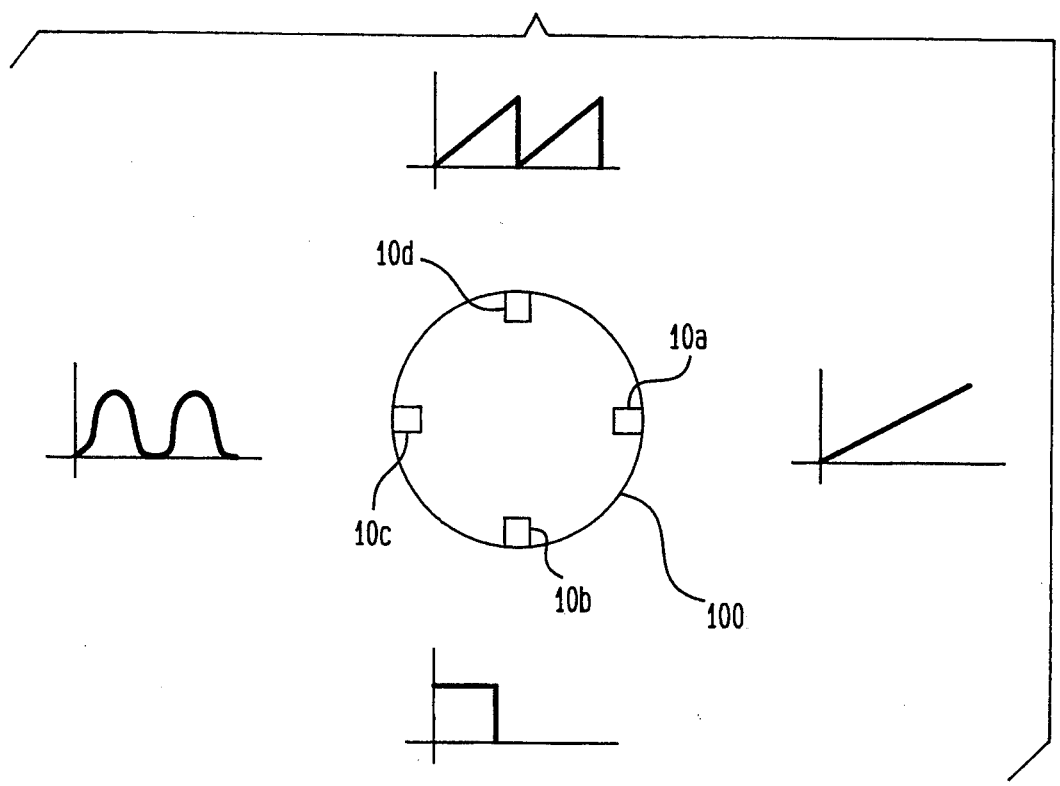
FIG. 1A is an end view of an axial symmetric structure having a plurality of acoustic radiator devices placed radially therearound.
Figure 1B:
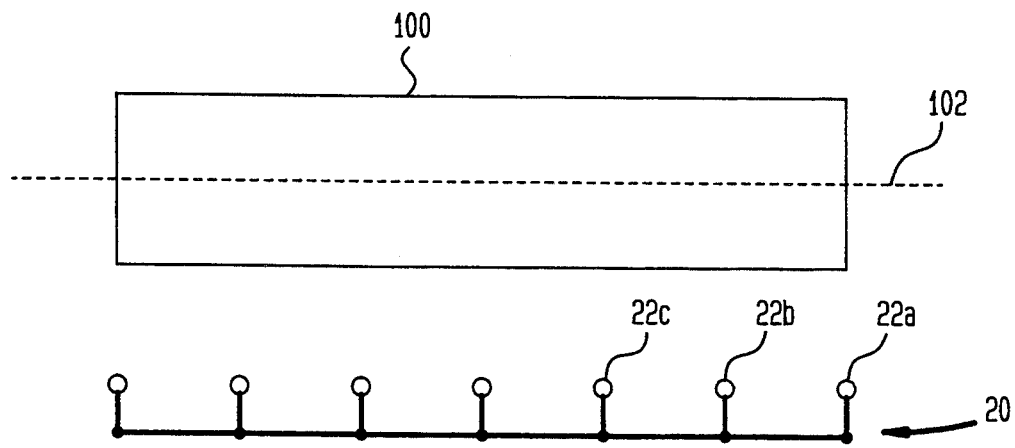
FIG. 1B is a side view of the structure of FIG. 1A having a one-dimensional measurement array located in its acoustic near field.

Referring now to the drawings, and more particularly to FIGS. 1A and 1B, the method of mapping the acoustic near field according to the present invention will be described. For sake of clarity, the elements of FIG. 1A have been limited to the excitation aspect of the present invention while the elements shown in FIG. 1B have been limited to the measurement aspect of the present invention. In FIG. 1A, an end view is shown of axial symmetric structure 100 such as a cylinder or drum with a plurality (only four are shown for ease of description) of structural excitation (i.e., vibration) devices 10a–10d positioned radially around the perimeter of structure 100. Once positioned, structure 100 and devices 10a–10d are not moved throughout the mapping process. Structural excitation devices 10a–10d may be speakers or shakers and may be located either internally or externally with respect to structure 100.

In FIG. 1B, a side view is shown of structure 100 with a line array 20 of acoustic wave measuring devices 22a, 22b, ... placed in the acoustic near field of structure 100. Line array 20 is placed to conform to the surface of structure 100 along its longitudinal axis 102. Once positioned, array 20 is not moved throughout the mapping process. Acoustic wave measuring devices 22a, 22b, ... may be any of the well known acoustic measurement devices such as hydrophones, microphones, accelerometers, etc.

In operation, each structural excitation device 10a–10d excites structure 100 either by direct contact or indirect energy transfer depending on the positioning/type of devices used. By way of non-limiting illustrative example, device 10a is excited in accordance with a ramp function, device 10b is excited in accordance with a step function, device 10c is excited with a sine function and device 10d is excited with a sawtooth function. (More realistically, three examples of an excitation profile might include random noise excitation, circumferential mode excitation and point excitation. With random noise excitation, each device produces a different non-correlated signal. With circumferential mode excitation, the circumferential modes of the axial symmetric structure are excited. The modes of a structure are a means of describing the frequency dependent motion of the structure. With point excitation, only one of the plurality of structural excitation devices receives a non-zero signal.)

Once structure 100 is excited by devices 10a–10d, measuring devices 22a, 22b, ... are sampled. This results in a surface conforming map of the acoustic near field due to the specific excitation energy profile delivered by devices 10a–10d along the fixed position line array 20. To obtain a complete map of the acoustic near field without moving either devices 10–10d or devices 22a, 22b, ..., the excitation energy profile is rotated. To rotate this energy profile, the particular set of functions used to excite devices 10a–10d is incrementally shifted clockwise (or counterclockwise). In other words, in terms of a clockwise shift or rotation, device 10a is next excited with the sawtooth function, device 10b is next excited with the ramp function, etc. Measurement devices 22a, 22b, ... are then sampled again to yield a second surface conforming map of the acoustic near field at the fixed position of line array 20. Thus, a complete map of the acoustic near field based on the specific excitation energy profile can be obtained by merely shifting or rotating the energy profile around structure 100.

Figure 2A:
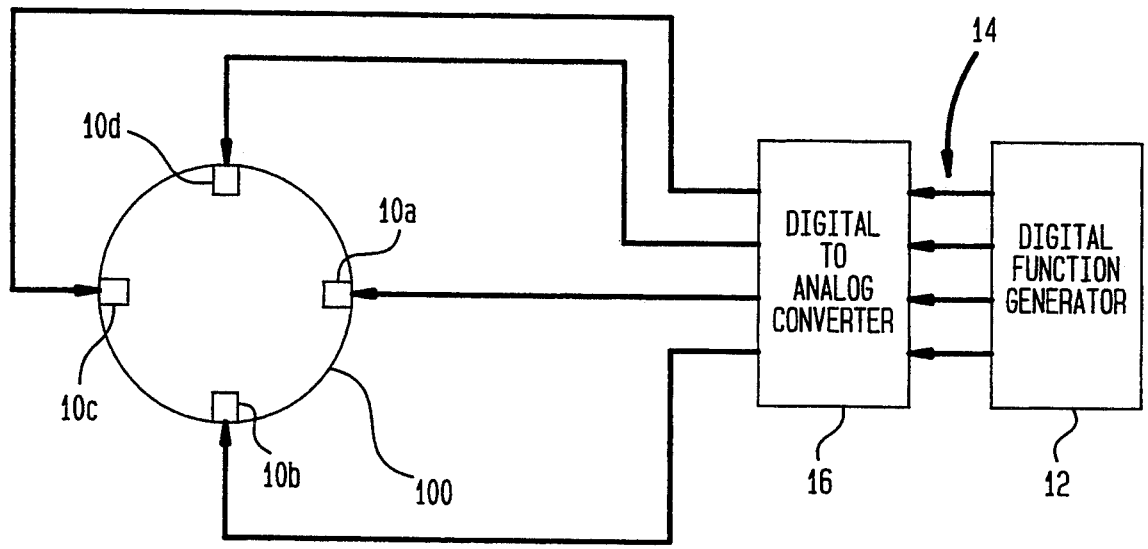
FIG. 2A is a schematic view of a preferred embodiment excitation system according to the present invention.

A representative system for implementing the method of the present invention will now be described with reference to FIGS. 2A and 2B where, once again, the excitation aspect will be described with the aid of FIG. 2A and the measurement aspect will be described with the aid of FIG. 2B. In FIG. 2A, a digital function generator 12 (e.g., a computer) outputs a plurality (four for the example shown) of digital representations of the particular excitation functions as described above onto a plurality of transmission channels 14. Note that it is preferable to initiate the excitations in a digital format to insure repeatability when the excitation functions are shifted or rotated. Each of the digital representations is passed through a multi-channel digital-to-analog converter 16 where the resulting analog excitation functions are provided to respective devices 10a–10d. Rotation of the functions is achieved by incrementally shifting the digital representations of the excitation functions on transmission channels 14.

Figure 2B:
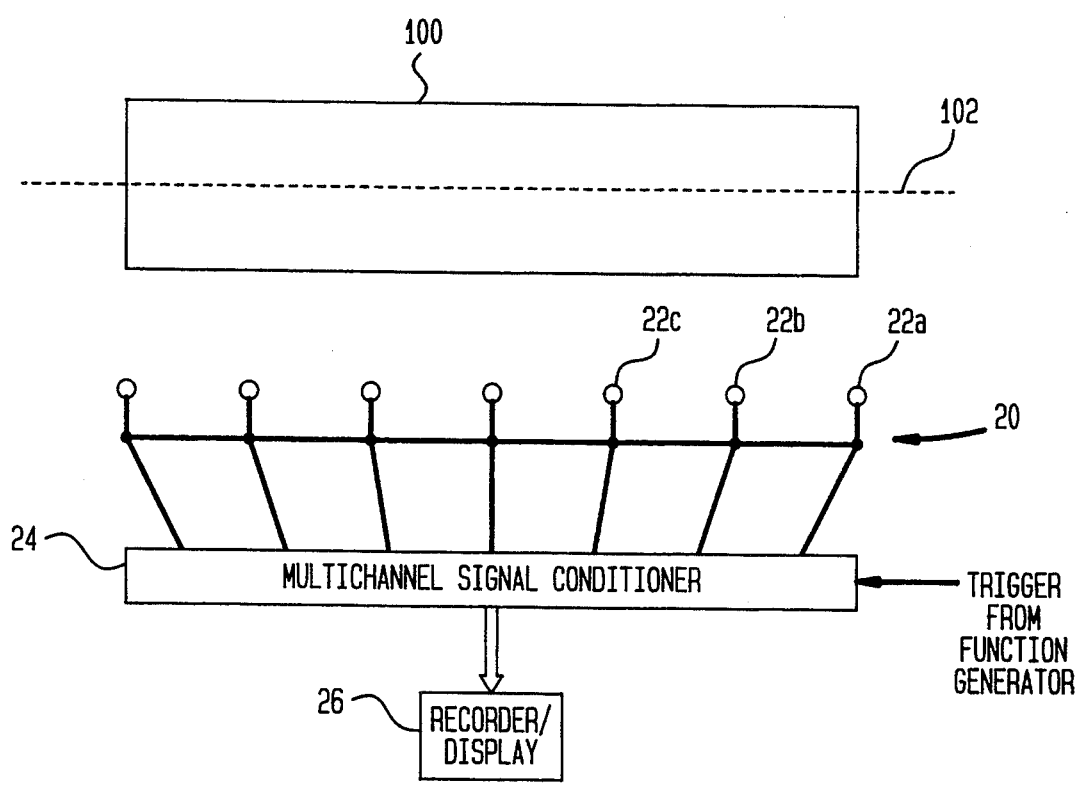
FIG. 2B is a schematic view of a preferred embodiment measurement system according to the present invention.

In FIG. 2B, outputs of devices 22a, 22b, ... are fed to a multi-channel signal conditioner 24. Functions provided by conditioner 24 might include filtering, analog-to-digital conversion, amplification, etc. according to processes and means well known in the art. To insure that data is sampled only when structure 100 is excited in accordance with the specific excitation energy profile, conditioner 24 could be enabled by a trigger pulse issued from digital function generator 12 each time the energy profile is shifted and transmitted over transmission channels 14. The sampled data from array 20 may be recorded or displayed on a recorder/display 26 as is well known in the art. Once again, a mapping of the acoustic near field of structure 100 is synthesized as the specific excitation energy profile shifts or rotates around through each of devices 10a–10d.

Figure 3:
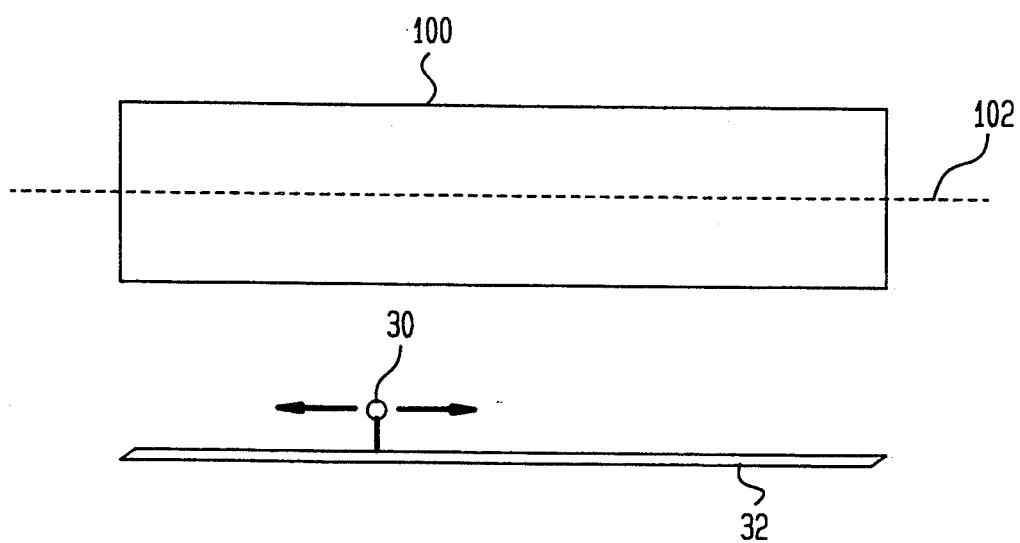
FIG. 3 is a schematic view of an alternative measurement system.

While the present invention has been described relative to a particular embodiment, it is not so limited. For example, measurements of data could be carried out by a single measurement device as opposed to a line array of measurement devices. As shown in FIG. 3, a single measurement device 30 could be moved along a stationary surface conforming track 32 that conforms to the surface of structure 100 along its longitudinal axis 102. Movement of device 30 could be manual or by means of a motor (not shown). In such an embodiment, the specific excitation energy profile would be repeated for each location along track 32 for which measurement is desired. However, the ordering of steps is not important. Device 30 could complete one longitudinal scan along track 32 for a given excitation profile and then the excitation function could be shifted or rotated. Alternatively, the excitation functions could be shifted or rotated to all transmission channels and measurements taken before device 30 is moved to a new position along track 32.

Figure 4A:
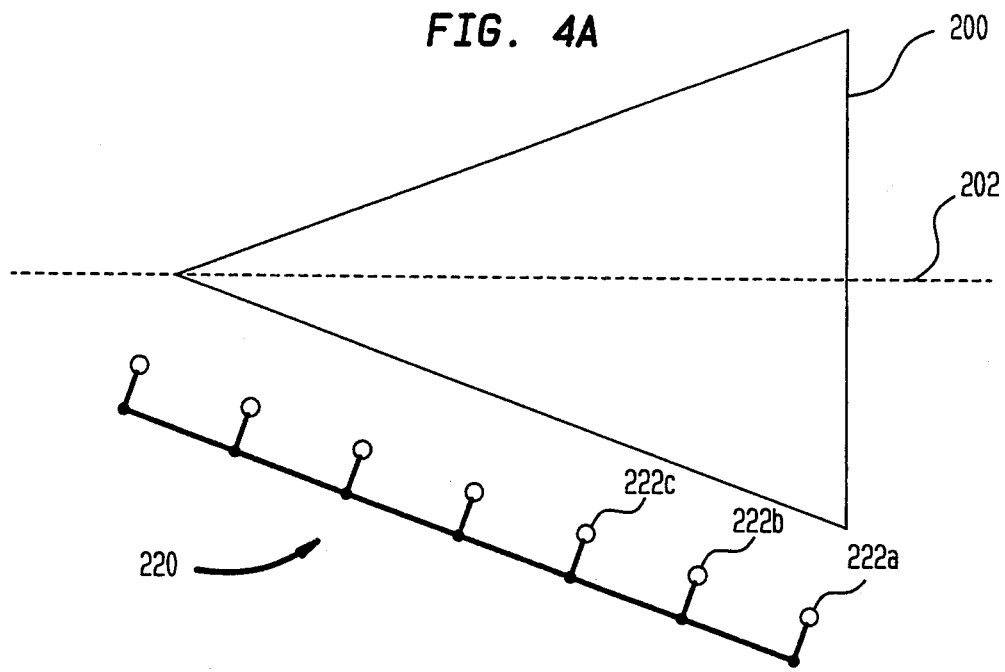
FIG. 4A depicts a line array of measurement devices conforming to a longitudinal surface of a conical structure.
Figure 4B:
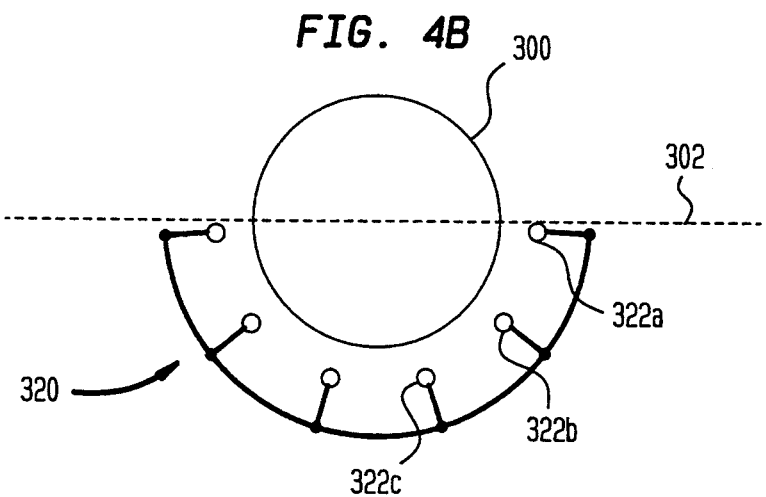
FIG. 4B depicts a line array of measurement devices conforming to a surface of a spherical structure.
Figure 4C:
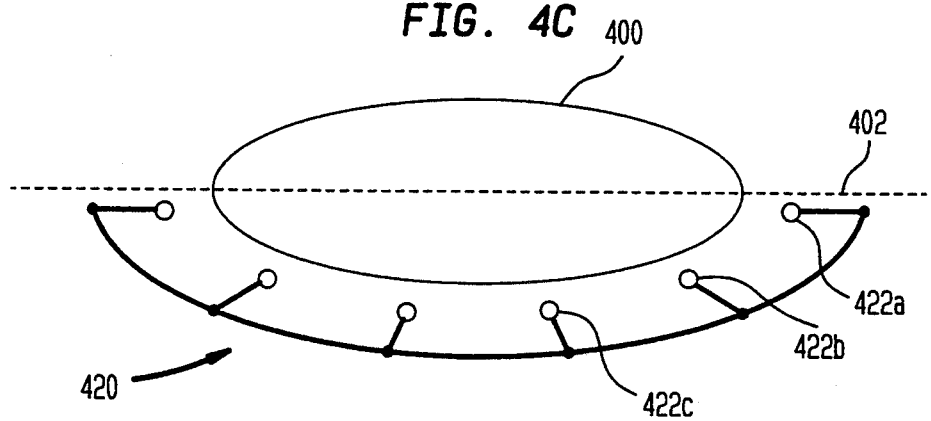
FIG. 4C depicts a line array of measurement devices conforming to a longitudinal surface of a prolate spherical structure.

The present invention is applicable to any axial symmetric structure such as cones, spheres and prolate spheres. Just as in the example described above, the line array of measurement devices (or stationary track for guiding the movement of a single measurement device) is placed in the acoustic near field of the structure and conforms to the structure's longitudinal surface. To illustrate this, FIG. 4A depicts a line array 220 of measurement devices 222a, 222b, ... that conforms to the surface of conical structure 200 along its longitudinal axis 202. In FIG. 4B, line array 320 is a curvilinear array of measurement devices 322a, 322b, ... that conforms to the surface of spherical structure 300 along its axis 302. In FIG. 4C, line array 420 again is a curvilinear array of measurement devices 422a, 422b, ... that conforms to the surface of prolate spherical structure 400 along its longitudinal axis 402.

Figure 5:
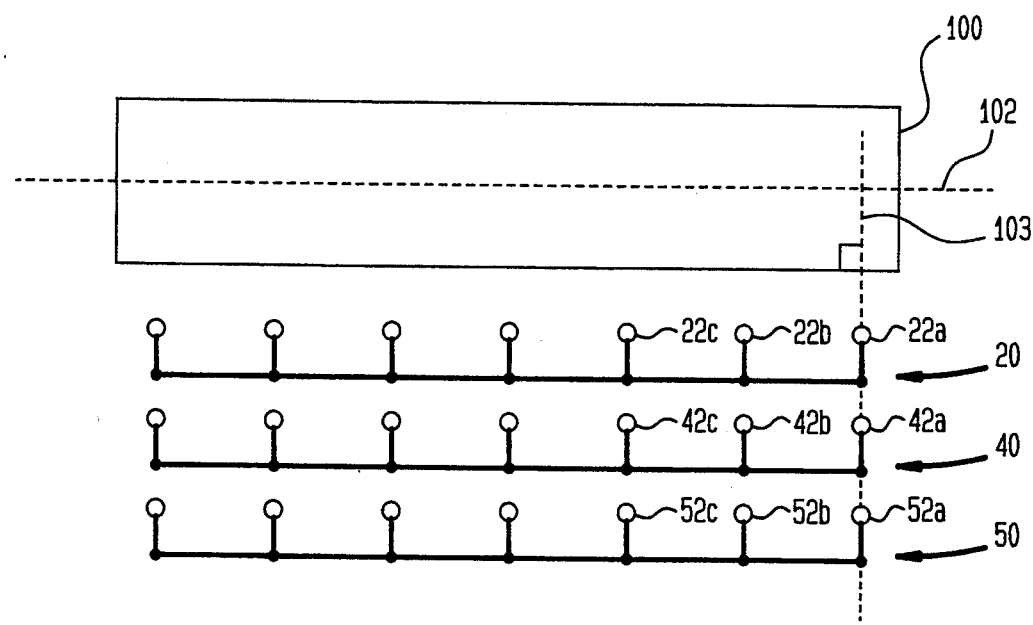
FIG. 5 depicts the embodiment of FIG. 1B extended to a multiple-tier measurement arrangement.

In addition, the present invention may be extended to provide a multiple-tier map of the acoustic near field. Each tier conforms to a longitudinal surface of the structure. The tiers are maintained in a spaced apart, parallel relationship with one another in the same plane such that each tier measures the acoustic near field of the structure at a different distance from the structure. By way of illustrative example, an extension of the embodiment of FIG. 1B to three tiers is shown in FIG. 5. Line array 20 forms the first tier (nearest structure 100), line array 40 forms the second tier, and line array 50 forms the third tier (furthest from structure 100). Additional (or fewer) tiers may be provided as needed. For ease of processing, measurement devices may be aligned along surface normal vectors, e.g., measurement devices 22a, 42a and 52a are aligned along the surface normal vector represented by dotted line 103. However, it is to be understood that alignment of each tier's measurement devices is not a requirement of the present invention.

Figure 6A:
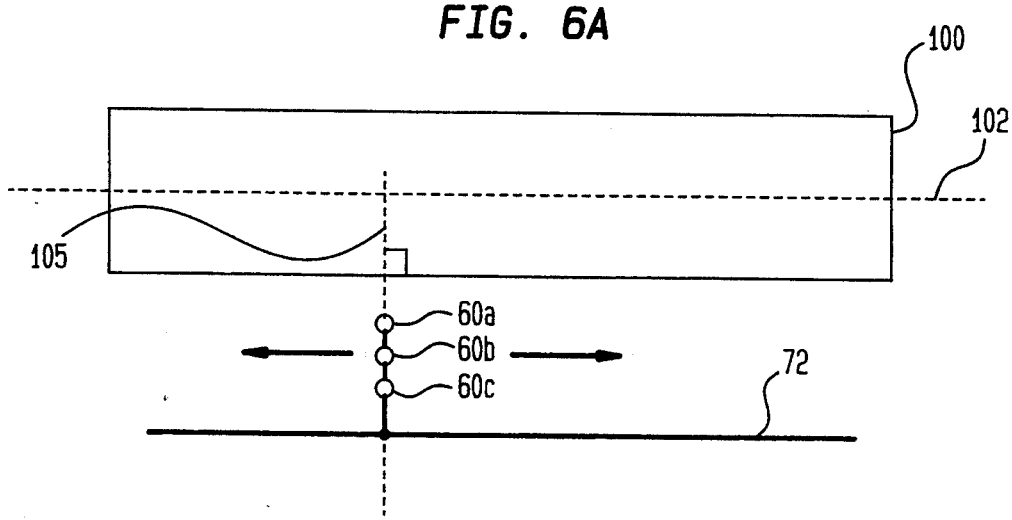
FIG. 6A is the multiple-tier arrangement of FIG. 5 implemented with a moving one-dimensional measurement device.
Figure 6B:
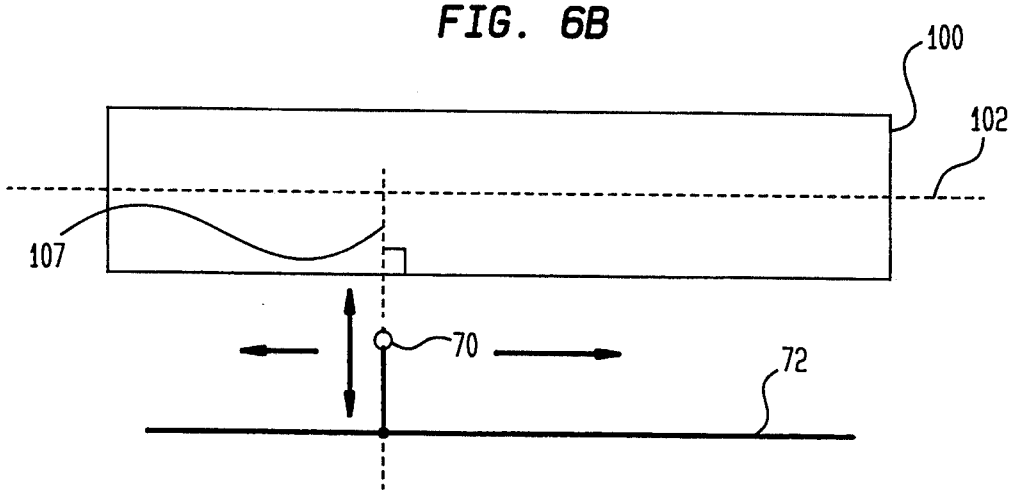
FIG. 6B is the multiple-tier arrangement of FIG. 5 implemented with a point measurement device capable of movement in two dimensions.

The multiple-tier arrangement of FIG. 5 may also be implemented as shown in FIG. 6A by three measurement devices 60a, 60b and 60c capable of one-dimensional movement as a unit along surface conforming track 62. Each device is aligned along the surface normal vector represented by dotted line 105 and is a unique distance away from the surface of structure 100. Alternatively, a single measurement device 70 could be moved two-dimensionally, i.e., along surface conforming stationary track 72 as well as along the surface normal vector represented by dotted line 107.

The advantages of the present invention are numerous. No complex coordinated movements are required between the scanning system and the structure to be evaluated. Rather, a synthetic rotation of the structure is achieved by rotating the excitation energy profile used to generate the acoustic near field response. This reduces the cost of design, construction and operation for acoustic near field mapping of axial symmetric structures.

Although the invention has been described relative to a specific embodiment thereof, there are numerous variations and modifications that will be readily apparent to those skilled in the art in the light of the above teachings. It is therefore to be understood that, within the scope of the appended claims, the invention may be practiced other than as specifically described.

What is claimed is:

1. A method of mapping the acoustic near field of an axial symmetric structure, comprising the steps of:
    generating a set of repeatable excitation signals for transmission over a corresponding set of channels;
    converting each repeatable excitation signal from said set of repeatable excitation signals to excitation energy at an excitation source site from a corresponding set of excitation source sites located radially around said structure;
    measuring the acoustic near field of said structure due to said excitation energy along a line that conforms to a longitudinal surface of said structure; and
    repeating said steps of converting and measuring as said set of repeatable excitation signals is incrementally shifted around said set of excitation source sites, wherein said mapping of the acoustic near field is complete when each said excitation source site has produced said excitation energy corresponding with each said repeatable excitation signal.

2. A method according to claim 1 wherein said step of measuring is accomplished at a single measuring time with a stationary line array of measurement devices.

3. A method according to claim 1 wherein said step of measuring is accomplished over a period of time with a single measurement device traversing said line that conforms to said longitudinal surface.

4. A method of mapping the acoustic near field of an axial symmetric structure, comprising the steps of:
    providing a plurality of excitation signals;
    subjecting said structure to excitation energy based on said excitation signals at a plurality of stationary excitation sites located radially around said structure; and
    measuring the acoustic near field of said structure due to said excitation energy along a line that conforms to a longitudinal surface of said structure, wherein said step of measuring takes place as each of said plurality of excitation signals is incrementally provided to each of said plurality of stationary excitation sites and wherein said mapping of the acoustic near field is complete when each of said plurality of excitation signals has been provided to each of said plurality of stationary excitation sites.

5. A method according to claim 4 wherein said stationary excitation sites are in a one-to-one correspondence with said plurality of excitation signals.

6. A method according to claim 4 wherein said step of measuring is accomplished at a single measuring time with a stationary line array of measurement devices.

7. A method according to claim 4 wherein said step of measuring is accomplished over a period of time with a single measurement device traversing said line that conforms to said longitudinal surface.

8. A method of mapping the acoustic near field of a stationary axial symmetric structure, comprising the steps of:
    subjecting said structure to a excitation energy profile, which rotates from a plurality of stationary excitation sites located radially around said structure; and
    measuring the acoustic near field of said structure due to said rotating excitation energy profile along at least one line that conforms to a longitudinal surface of said structure, wherein said mapping of the acoustic near field is complete when one rotation of said rotating excitation energy profile is complete.

9. A method according to claim 8 wherein said step of measuring is accomplished at a single measuring time with at least one stationary line array of measurement devices.

10. A method according to claim 8 wherein said step of measuring is accomplished over a period of time with a single measurement device traversing said at least one line that conforms to said longitudinal surface.

11. A method according to claim 8 wherein said step of measuring occurs on a plurality of lines, each of said plurality of lines conforming to said longitudinal surface, each of said plurality of lines residing in the same plane and being maintained in a spaced apart, parallel relationship with one another.

12. A system for mapping the acoustic near field of an axial symmetric structure, comprising:
    means for subjecting said structure to a excitation energy profile, which rotates from a plurality of stationary excitation sites located radially around said structure; and
    means for measuring the acoustic near field of said structure due to said rotating excitation energy profile along at least one line that conforms to a longitudinal surface of said structure, wherein said mapping of the acoustic near field is complete when one rotation of said rotating excitation energy profile is complete.

13. A system as in claim 12 wherein said means for subjecting said structure to a rotating excitation energy profile comprises:
    a signal generator for generating a set of repeatable excitation signals for transmission over a corresponding set of channels;
    a structural excitation means connected to each of said corresponding set of channels and located at each of said plurality of stationary excitation sites for converting each repeatable excitation signal from said set of repeatable excitation signals to excitation energy, wherein said rotating energy profile is created as said set of repeatable excitation signals is incrementally provided to each said structural excitation means located at each of said plurality of stationary excitation sites.

14. A system as in claim 12 wherein said means for measuring the acoustic near field comprises at least one stationary line array of measurement devices.

15. A system as in claim 12 wherein said means for measuring the acoustic near field comprises a single measurement device capable of moving along said at lest one line that conforms to said longitudinal surface of said structure.

16. A system as in claim 12 wherein said means for measuring are located on a plurality of lines, each of said plurality of lines conforming to said longitudinal surface, each of said plurality of lines residing in the same plane and being maintained in a spaced apart, parallel relationship with one another.

* * * * *